United States Patent [19]

Nagahama et al.

[11] Patent Number: 4,898,882
[45] Date of Patent: Feb. 6, 1990

[54] RESISTANCE IMPARTING AGENT FOR COLD SYNDROME OF LOW PULMONARY FUNCTION PATIENTS

[75] Inventors: Fumio Nagahama, Sapporo; Norihiro Kakimoto, Machida; Kohei Miyao, Tokyo, all of Japan

[73] Assignee: Asai Germanium Research Institute, Tokyo, Japan

[21] Appl. No.: 284,848

[22] Filed: Dec. 12, 1988

Related U.S. Application Data

[63] Continuation of Ser. No. 869,698, Jun. 2, 1986, abandoned.

[51] Int. Cl.$^4$ .............................................. A61K 31/28
[52] U.S. Cl. ..................................... 514/492; 514/849
[58] Field of Search ......................................... 514/492

[56] References Cited

U.S. PATENT DOCUMENTS 4,229,468  10/1980  Miyao et al. ......................... 514/492

OTHER PUBLICATIONS

Chemical Abstracts 80:104171z, 1974 (Asai et al.).

*Primary Examiner*—Leonard Schenkman
*Attorney, Agent, or Firm*—Burns, Doane, Swecker & Mathis

[57] ABSTRACT

Administration of a resistance imparting agent characterized by comprising an organogermanium compound as an effective component shown by the following formula (I);

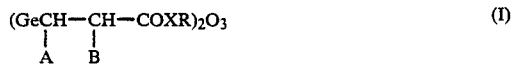

(wherein A and B denote hydrogen or lower alkyl groups such as methyl and ethyl groups, R denotes a combination of one or two atoms or groups shown by A or B, and X denotes an oxygen or nitrogen atom) in patients having low pulmonary function (35 examples of a group to which the agent was administered, 34 examples of an untreated group) showed that the number complaining of cold syndrome was 13 in the first group and 30 in the second group, which the total number of days during which remedies were used by the first group for cold syndrome was 79 days (of a total possible of 4635 days) compared with 295 days (of a total possible of 4860 days) for the untreated group, and that patients having low pulmonary function were apparently endowed with resistance to cold syndrome. Furthermore, no remarkable side-effects were observed.

9 Claims, No Drawings

RESISTANCE IMPARTING AGENT FOR COLD SYNDROME OF LOW PULMONARY FUNCTION PATIENTS

This application is a continuation of application Ser. No. 869,698, filed June 2, 1986, abandoned.

BACKGROUND OF THE INVENTION

1. Field of the Invention

The present invention relates to a resistance imparting agent for the cold syndrome of a patient having low pulmonary function, and which particularly relates to a resistance endower for cold syndrome of patients having low pulmonary function comprising a particular organogermanium compound as an effective component.

2 Prior Art

Patients with low pulmonary function, for example, pneumoconiosis patients having extreme pulmonary functional illness (patients concluded to be Control 4 in the Pneumoconiosis law) easily catch the cold syndrome, generally called a "cold," and are hard to cure once they catch a cold, sometimes resulting in a deteriorating condition of respiratory insufficiency symptom and rapid deterioration of recuperation, and leading to death.

Therefore, for low pulmonary function patients, for example, pneumoconiosis patients having extreme pulmonary functional illness concluded to be Control 4 in the Pneumoconiosis law, a complaint of a slight "cold" or "a touch of cold" cannot be ignored and it is of upmost importance to impart resistance to a cold syndrome to such patients so as to make it hard for them to catch the cold syndrome.

However, since there has so far been no medicine capable of being used for the above-described purpose, no preventive treatment for imparting resistance to the cold syndrome has been carried out for the purpose of making it difficult for patients to catch the cold syndrome. Instead a method for cure normally has been carried out in which antibiotics or others drugs have been administered after the patient has actually caught the cold syndrome.

SUMMARY OF THE INVENTION

It is, therefore, a main object of the present invention to provide a resistance imparting agent capable of imparting effective resistance to the cold syndrome to low pulmonary function patients.

It is another object of the present invention to provide a resistance imparting agent capable of imparting resistance to the cold syndrome to low pulmonary function patients without causing any side-effects.

The composition employed in the present invention for the above-described objects is mainly characterized by comprising an organogermanium compound as an effective component shown by the following formula (I):

(wherein A and B denote hydrogen or lower alkyl groups such as methyl and ethyl groups, R denotes a combination of one or two atoms or groups shown by A or B, and X denotes an oxygen or nitrogen atom).

DETAILED DESCRIPTION OF THE INVENTION

The present invention relates to a resistance imparting agent for the cold syndrome for administration to low pulmonary function patients, wherein "low pulmonary function patients" means those with pulmonary function which is deteriorated by chronic obstructive pulmonary emphysema or pneumoconiosis.

The present invention also relates to such a resistance imparting agent incorporating a particular organogermanium compound as an effective component. This organogermanium compound, as shown by the above formula (I), has a substituted germyl propionic acid derivative as a fundamental structure in which a propionic acid residue having an oxygen functional group COXR and substituents A and B is bonded to a germanium atom and is a molecular compound in which the substituted germyl propionic acid derivatives and oxygen atoms are alternatively bonded in a ratio of 2:3. The substituents A and B denote hydrogen atoms or lower alkyl groups such as methyl and ethyl groups, R denotes a combination of one or two hydrogen atoms or the lower alkyl groups shown by A and B, and X denotes oxygen or nitrogen atom.

The germanium atom itself has long been investigated as a semiconductor, but investigations with respect to its organic compounds have recently proceeded, results of such investigations have been actively published and, consequently, the organic compounds have attracted great attention.

For example, it has been reported that carboxyethylgermanium sesquioxide $(GeCH_2CH_2COOH)_2O_3$ and other organogermanium compounds included in the above formula (I) have strong inhibitive actions on a particular enzyme and show antioxidative actions (U.S. Pat. No. 4,720,564), but there has been no application for imparting resistance to cold syndrome to patients having low pulmonary function, as in the present invention.

The organogermanium compound used as an effective component of the present invention having the above-described chemical structure can be synthesized by various methods. For example, trichlorogermane (II) is added to an unsaturated compound (III) having the substituents A and B to obtain a 3-trichlorogermyl propionic acid derivative (IV) and the Ge-Cl bonds thereof are hydrolyzed.

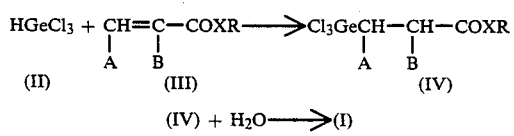

The organogermanium compound obtained in such a manner as an effective component of the present invention is a colorless and transparent crystal and the resistance imparting agent for the cold syndrome of the present invention is prepared in various forms such as a tablet, a capsule or a powder in accordance with a conventional method.

The obtained resistance imparting agent for cold syndrome of the present invention was administered to for example, pneumoconiosis patients having extreme pulmonary function illnesses (patients concluded to be Control 4 on the Pneumoconiosis law), and the number complaining of cold syndrome, the total number of days during which remedies were used for cold syndrome, and the frequency of cold syndrome were examined for this group. It was thereby confirmed that the group to which the agent of the present invention was administered showed a distinct difference from another group which was not given the agent of this invention and that the agent of the present invention can impart resistance to the cold syndrome in patients having low pulmonary function and can prevent them from catching the cold syndrome.

DESCRIPTION OF PREFERRED EMBODIMENT

1. Synthesis of organogermanium compound 50.4 9 (0.2 mol) of 3-trichlorogermyl propionic acid which was synthesized by a known method and showed the same physical and chemical characteristics as those described in the references was added to 500 ml of water, agitated for 1 hour, and then allowed to stand for 24 hours. The crystals precipitated were filtered and recrystallized to obtain 28.0 g of colorless crystals of carboxyethylgermanium sesquioxide [a compound of the above-described formula (I) in which $A=B=R=H$ and $X=01$ ]showing the same physical and chemical characteristics as those described in the references at a yield of 83.3 %.

2. Example of imparting resistance to cold syndrome in patients having low pulmonary function (1) Method Capsules or apparently similar capsules containing the agent of the present invention incorporating the above-synthesized organogermanium compound as an effective component in an amount of 250 mg. per capsule were administered to 69 patients mainly comprising patients concluded to be Control 4 in the Pneumoconiosis law and 2 patients suffering from chronic obstructive pulmonary emphysema in doses of 3 capsules at a time after meals, 3 times a day, on the basis of the predetermined code table. In the patients having pneumoconiosis, the treated group comprised 34 patients while another untreated group comprised 33 patients.

The administration period was in the winter during which the patients would easily catch the cold syndrome and was established to be 3 such periods over the course of 3 years. The patients were grouped into the two groups after the completion of administration in accordance with the above code table. There was no difference in the sex of the patients to be examined as they were all men and and there was also no significant difference between the two groups with respect to age distribution, past business career, commencement of the examination, or period of taking medicine.

(2) Observation items

The patients recorded the frequency of phlegm occurrence, body temperature, and whether or not they had a slight cold and doctors observed separately and recorded the frequency of occurrence of the cold syndrome, the number having a fever of above 37C., the number of days during which cold remedies (including antibiotics) were used, the frequency of cold syndrome, langour throughout the body, loss of appetite or otherwise, anhelation, and cardiopalmus.

(3) Results

The total number of experiences of cold syndrome during the period of the administration was, as seen from the table below, 30 for the patients in the group in which the agent of the present invention was not administered, but only 13 for the patients in which the agent of the present invention was administered, thus showing a significant difference of $P<0.001$ between these two sets of results.

The table described below shows the results for all patients except those who died during the examination period and those complaining of diarrhea after taking the agent.

TABLE

| Period | Untreated group | | | Treated group | | |
| --- | --- | --- | --- | --- | --- | --- |
| | Administration period | Patients number | Cold time | Administration period | Patients number | Cold time |
| (1) | 4.0 months | 2 | 3 | 4.0 months | 0 | 0 |
| | 4.5 months | 5 | 4 | 4.5 months | 7 | 0 |
| | 6.5 months | 5 | 8 | 6.5 months | 6 | 5 |
| (2) | 3.5 months | 3 | 0 | 3.5 months | 4 | 1 |
| | 6.0 months | 1 | 2 | 5.0 months | 3 | 0 |
| | 6.5 months | 5 | 4 | 6.5 months | 1 | 0 |
| (3) | 3.5 months | 9 | 4 | 3.5 months | 12 | 7 |
| | 4.0 months | 0 | 0 | | | |
| | 6.0 months | 2 | 3 | | | |
| | 6.5 months | 1 | 2 | 6.5 months | 1 | 0 |
| Total | | 33 | 30 | | 34 | 13 |

For the patients suffering from chronic obstructive pulmonary emphysema, those patients to which the agent of the present invention (1 second rate 43.8 %) was administered experienced no cold syndrome, while the patients to which the agent of the present invention (1 second rate 33.6 %) was not given experienced a cold syndrome twice and therefore took a remedy.

Next, with respect to the number of patients having a fever of above 37° C. and the number of days in which cold remedies (including antibiotics) were used, the total number experiencing fever was many, namely 109, in the untreated group, while it was only 67 in the treated group, and the number of days during which cold remedies (including antibiotics) was used was 319 days in the former group, while it was only 79 days in the latter group. There was thus a significant difference of $P<0.01$ for the numbers of experiencing a fever and of $P<0.001$ for the number of days during which cold remedies were used on comparing these values.

Furthermore, when the frequency of the cold syndrome was investigated, it was 19 among the 33 examples in the untreated group, while it was only 10 among the 34 examples in the treated group. It was thus apparent that it was harder for the first group of patients in which the agent of the present invention was administered to catch the cold syndrome than it was for the untreated group (in this case, the difference was $P<0.05$).

In addition, during the whole administration period, the average values for the number of white blood corpuscles and the peripheral blood lymph cells in the administrated group were higher than in the untreated group, while the average values the numbers of red blood corpuscles, the Hb amount, and the erythrocyte sedimentation rate values were the same in both groups.

On the other hand, symptoms of which the patients themselves complain include langour throughout the whole body, loss of appetite, anhelation, cardiopalmus, and cyanosis, for example. Patients who had initially complained of langour throughout their body did not complain of it during the administration and 5 patients in the treated group experienced improvement in this respect. Thus, there was a tendency for the group to which the agent of the present invention was administered to improve with regard to these symptoms.

In addition, although some patients complained of diarrhea, the agent of the present invention showed no noticeable side-effects.

We claim:

1. A method for treating or imparting resistance to a cold syndrome in a patient having low pulmonary function, said method comprising administering an effective amount to treat a cold syndrome of an organogermanium compound having the formula:

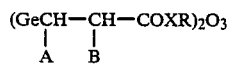

wherein A and B independently represent a hydrogen atom or a lower alkyl group, R represents a combination of one or two atoms or groups as identified above by A and B, and X represents an oxygen or nitrogen atom and a pharmaceutically acceptable carrier.

2. The method as claimed in claim 1 wherein said lower alkyl group is a methyl or ethyl group.

3. The method as claimed in claim 1 wherein A is a hydrogen atom.

4. The method as claimed in claim 1 wherein B is a hydrogen atom.

5. The method as claimed in claim 1 wherein X is an oxygen atom.

6. The method as claimed in claim 1 wherein R is a hydrogen atom.

7. The method as claimed in claim 1 wherein said patient has low pulmonary function due to chronic obstructive pulmonary emphysema.

8. The method as claimed in claim 1 wherein said patient has low pulmonary function due to pneumoconiosis.

9. A method for treating or imparting resistance to a cold syndrome in a patient having low pulmonary function, said method comprising administering an effective amount to treat a cold syndrome of an organogermanium compound having the formula $(GeCH_2CH_2COOH)_2O_3$ and a pharmaceutically acceptable carrier.

* * * * *